(12) United States Patent
Martinelli et al.

(10) Patent No.: US 6,409,729 B1
(45) Date of Patent: Jun. 25, 2002

(54) CLAMP ASSEMBLY FOR AN EXTERNAL FIXATION SYSTEM

(75) Inventors: Orlando Martinelli, Bern; Beat Inauen, Hölstein; Erwin Flühler, Allschwil, all of (CH); Lutz Claes, Neu-Ulm (DE); Heinz Gerngross, Ulm (DE); Götz Rübsaamen, Traunstein (DE)

(73) Assignee: Synthes (USA), Paoli, PA (US)

( * ) Notice: Subject to any disclaimer, the term of this patent is extended or adjusted under 35 U.S.C. 154(b) by 0 days.

(21) Appl. No.: 09/714,990

(22) Filed: Nov. 20, 2000

Related U.S. Application Data

(63) Continuation of application No. PCT/CH98/00207, filed on May 19, 1998.

(51) Int. Cl.$^7$ .............................................. A61B 17/64
(52) U.S. Cl. ....................................................... 606/59
(58) Field of Search ............................. 606/54, 57, 58, 606/59, 53; 403/54, 53, 164

(56) References Cited

U.S. PATENT DOCUMENTS

| | | |
|---|---|---|
| 4,135,505 A | 1/1979 | Day |
| 4,273,116 A | 6/1981 | Chiquet |
| 4,312,336 A | 1/1982 | Danieletto et al. |
| 4,483,334 A | 11/1984 | Murray |
| RE31,809 E | 1/1985 | Danieletto et al. |
| 4,548,199 A | 10/1985 | Agee |
| 4,600,000 A | 7/1986 | Edwards |
| 4,628,922 A | 12/1986 | Dewar |
| 4,662,365 A | 5/1987 | Gotzen et al. |

(List continued on next page.)

FOREIGN PATENT DOCUMENTS

| | | | |
|---|---|---|---|
| DE | 89 14 594 | 3/1990 | |
| EP | 0 011 258 | 5/1980 | |
| EP | 0 420 430 A1 | 4/1991 | |
| EP | 0 806 185 A1 | 11/1997 | |
| EP | 0 858 781 | 8/1998 | |
| EP | 0 913 128 A2 | 5/1999 | |
| FR | 2 557 933 | 7/1985 | |
| JP | 08-299361 | 11/1996 | |
| JP | 10-043204 | 11/1997 | |
| JP | 10-174695 | 5/1998 | |
| JP | 10-225465 | 8/1998 | |
| JP | 10-225466 | 8/1998 | |
| JP | 10-57397 | 4/1999 | |
| WO | 8302554 | * 8/1983 | .................. 606/59 |
| WO | WO92/12683 | 8/1992 | |
| WO | WO98/51227 | 11/1998 | |
| WO | WO99/25264 | 5/1999 | |

*Primary Examiner*—Eduardo C. Robert
*Assistant Examiner*—Nicholas L. Lucchesi
(74) *Attorney, Agent, or Firm*—Pennie & Edmonds LLP

(57) ABSTRACT

An external bone fixation system for clamping bone pins and a connecting element is provided. The system includes a jaw and an upper element for retaining bone pins therebetween, a middle element, and a lower element, with the elements being disposed about a common axis. The upper element swivels relative to the middle element, and the lower element rotates relative to the middle element. A borehole extending through the lower element permits demountable attachment of the device to the connecting element, as well as rotation thereabout. Opposing surfaces of at least two of the elements are positively engageable. The upper, middle, and lower elements are coupled by a common fastener disposed along the common axis, while the jaw and upper element are coupled by at least one fastener that is not disposed on the common axis. A single fastener can be used to arrest two or three degrees of freedom of movement.

37 Claims, 4 Drawing Sheets

U.S. PATENT DOCUMENTS

| | | | |
|---|---|---|---|
| 4,696,293 A | 9/1987 | Ciullo | |
| 4,714,076 A | 12/1987 | Comte et al. | |
| 4,848,368 A | * 7/1989 | Kronner | 128/92 Z |
| 4,895,141 A | 1/1990 | Koeneman et al. | |
| 4,919,119 A | 4/1990 | Jonsson et al. | |
| 4,998,935 A | 3/1991 | Pennig | |
| 5,108,394 A | 4/1992 | Kurokawa et al. | |
| 5,112,340 A | 5/1992 | Krenkel et al. | |
| 5,122,140 A | 6/1992 | Asche et al. | |
| 5,152,280 A | 10/1992 | Danieli | |
| 5,160,335 A | 11/1992 | Wagenknecht | |
| 5,207,676 A | 5/1993 | Canadell et al. | |
| 5,219,349 A | 6/1993 | Krag et al. | |
| 5,281,221 A | 1/1994 | Tadych | |
| 5,292,322 A | 3/1994 | Faccioli et al. | |
| 5,312,402 A | 5/1994 | Schlapfer et al. | |
| 5,320,623 A | 6/1994 | Pennig | |
| 5,342,360 A | 8/1994 | Faccioli et al. | |
| 5,376,090 A | 12/1994 | Pennig | |
| 5,380,322 A | 1/1995 | van den Brink et al. | |
| RE34,985 E | 6/1995 | Pennig | |
| 5,451,226 A | 9/1995 | Pfeil et al. | |
| 5,624,440 A | 4/1997 | Huebner | |
| 5,630,815 A | 5/1997 | Pohl et al. | |
| 5,643,262 A | 7/1997 | Metz-Stavenhagen et al. | |
| 5,683,389 A | 11/1997 | Orsak | |
| 5,693,053 A | 12/1997 | Estes | |
| 5,728,096 A | 3/1998 | Faccioli et al. | |
| 5,752,954 A | 5/1998 | Mata et al. | |
| 5,766,179 A | 6/1998 | Faccioli et al. | |
| 5,769,851 A | 6/1998 | Veith | |
| 5,785,709 A | 7/1998 | Kummer et al. | |
| 5,788,695 A | 8/1998 | Richardson | |
| 5,788,700 A | 8/1998 | Morawa et al. | |
| 5,797,908 A | 8/1998 | Meyers et al. | |
| 5,803,924 A | 9/1998 | Oni et al. | |
| 5,827,282 A | 10/1998 | Pennig | |
| 5,843,081 A | 12/1998 | Richardson | |
| 5,846,245 A | 12/1998 | McCarthy et al. | |
| 5,891,144 A | * 4/1999 | Mata et al. | 606/59 |
| 5,921,985 A | 7/1999 | Ross, Jr. et al. | |
| 5,928,230 A | 7/1999 | Tosic | |
| 5,941,877 A | 8/1999 | Viegas et al. | |
| 5,951,556 A | 9/1999 | Faccioli et al. | |
| 5,976,135 A | 11/1999 | Sherman et al. | |
| 6,022,348 A | 2/2000 | Spitzer | |
| 6,102,911 A | 8/2000 | Faccioli et al. | |
| 6,217,577 B1 | * 4/2001 | Hofmann | 606/57 |

* cited by examiner

CLAMP ASSEMBLY FOR AN EXTERNAL FIXATION SYSTEM

CROSS-REFERENCE TO RELATED APPLICATIONS

This application is a continuation of the U.S. National Stage designation of co-pending International Patent Application PCT/CH98/00207, filed May 19, 1998, the entire content of which is expressly incorporated herein by reference thereto.

FIELD OF THE INVENTION

The invention relates to a device for use in the external fixation of parts of broken bones. More particularly, the invention relates to an improved external fixation device that has positively locking joints and permits two or more rotational degrees of freedom to be detachably locked using a single component.

BACKGROUND OF THE INVENTION

A number of devices for use in the external fixation of bones are already known. One such device is disclosed in EP 0 011 258 A1 to ORTHOFIX, and includes an elongated middle body with two parts which are mutually displaceable along the body's longitudinal axis. Each of the parts of the middle body support a clamping unit for use in the insertion of nails or bone screws into a bone segment, and a push/pull device acts on both parts of the middle body. The clamps rest by means of universal joints, i.e. ball joints, on the outer ends of the displaceable parts of the middle body and thus permit the nails or screws that are insertable into the bone segments to pivot in three dimensions. This device has the drawback, however, that the clamps are only frictionally fixed in place, and as a result the slippage-resistance of the apparatus once fixed in place is substantially reduced.

Another device for the external fixation of bones using pins is disclosed in U.S. Pat. No. 5,160,335 to Wagenknecht. The affixation bar is optionally telescopable and fitted with clamps that hold bone the pins in place. Brackets are used to attach the clamping elements supporting the connecting parts to the fixation rod. The connecting parts permit three-way rotation of the clamping elements relative to the brackets. The device includes connecting components and clamps used in fastening the bone pins, as well as connecting components with curved support surfaces to affix the clamp elements of the clamps to the connecting components on the affixation bar. The connecting components are designed in such manner that the clamp elements can pivot in three degrees of freedom relative to the clamps. This device has the drawback that the pivot joints can only be affixed relative to one another in frictional manner, and furthermore three screws must be tightened to lock the clamp elements in place.

There exists a need for an improved external fixation device to confer a palliative effect. In particular, there exists a need for an improved external fixation device that enables affixation of the joints in geometrically locking, hereafter positively locking manner, and furthermore allows two or more rotational degrees of freedom to be detachably locked using a single tightening screw. The present invention provides an improved external fixation device that is capable of providing these improvements.

SUMMARY OF THE INVENTION

The present invention is related to an external bone fixation system for clamping bone pins and a connecting element. The system includes a jaw having top and bottom surfaces, and an upper element having top and bottom surfaces, with the jaw and upper element being configured and dimensioned for retaining bone pins therebetween. The system also includes a middle element having top and bottom surfaces, and a lower element having top and bottom surfaces. The elements are disposed about a common axis. The upper element can swivel relative to the middle element about a swivelling axis transverse to the common axis, and the bottom surface of the upper element is clampable against the top surface of the middle element. The lower element can rotate relative to the middle element about the common axis and the bottom surface of the middle element is clampable against the top surface of the lower element. The lower element has a borehole extending therethrough, and is demountably attachable to and rotatable about the connecting element. Opposing surfaces of at least two of the elements are positively engageable, and the upper, middle, and lower elements are coupled by a common fastener disposed along the common axis. The jaw and upper element are coupled by at least one fastener that is not disposed on the common axis.

In one embodiment, the common axis is disposed substantially perpendicular to the swivelling axis, and the borehole in the lower element is disposed transversely to the common axis. The top and bottom surfaces of the middle element are substantially parallel. The common fastener that couples the upper, middle, and lower elements also releasably fixes the lower element to the connecting element. In addition, the middle element includes a recessed portion with an insert seated therein, and the fastener threadably engages at least one of the insert and the lower element. The bottom surface of the upper element is curved and is received in a recess in the top surface of the middle element.

The bottom surface of the upper element and the recess in the top surface of the middle element include mutually positively locking serrations which lock the upper and middle elements in any one of a plurality of swivelled positions. Furthermore, the top surface of the lower element and the bottom surface of the middle element include mutually positively locking serrations which lock the lower and middle elements in any one of a plurality of rotational positions. The serrations can be radially disposed about the common axis. The lower element includes a fastener for demountably attaching that element to the connecting element. The borehole of the lower element is disposed about a central borehole axis that is offset from and transverse to the common axis.

The lower element can have a fastener hole that is aligned with the common axis and includes threads for engaging the threads of the common fastener. The upper element also can have a fastener hole aligned with the common axis which includes threads for engaging the threads of the common fastener. A single fastener can arrest two or three degrees of freedom. The fastener can be configured and dimensioned to be engaged at either of a first end and a second end and to permit screwing action thereof.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF PREFERRED EMBODIMENTS

Figure 1:
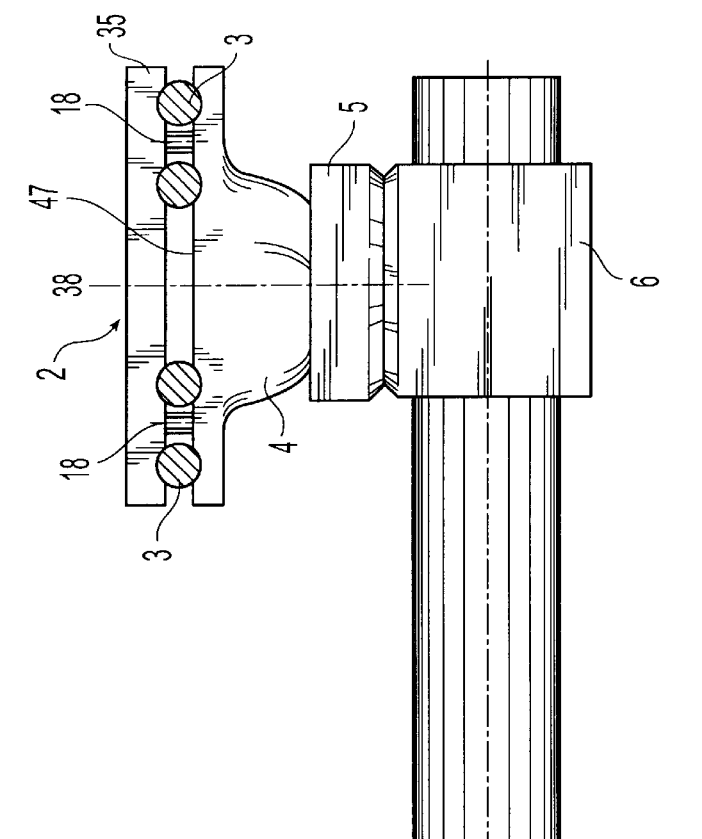
FIG. 1 is an elevational view of an embodiment of the present invention, with a connecting element having two clamp assemblies mounted thereon.
Figure 1:
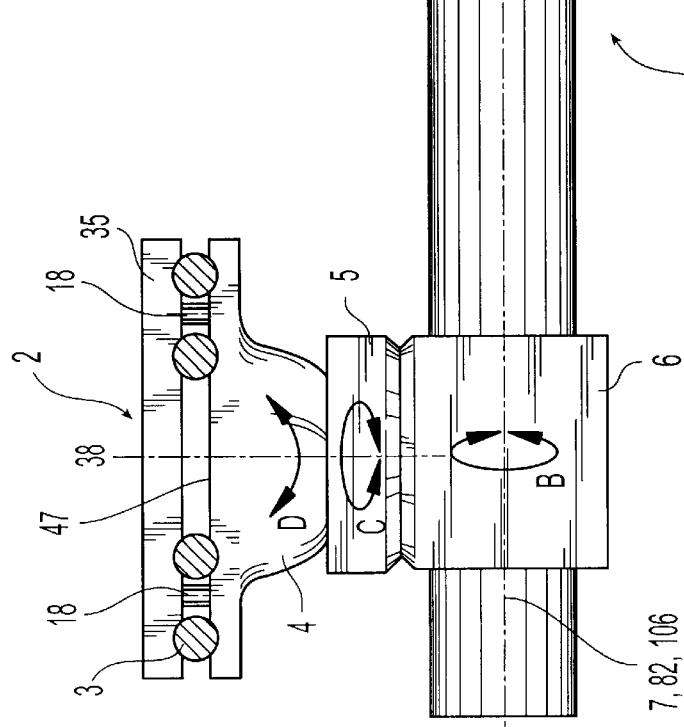
Figure 2:
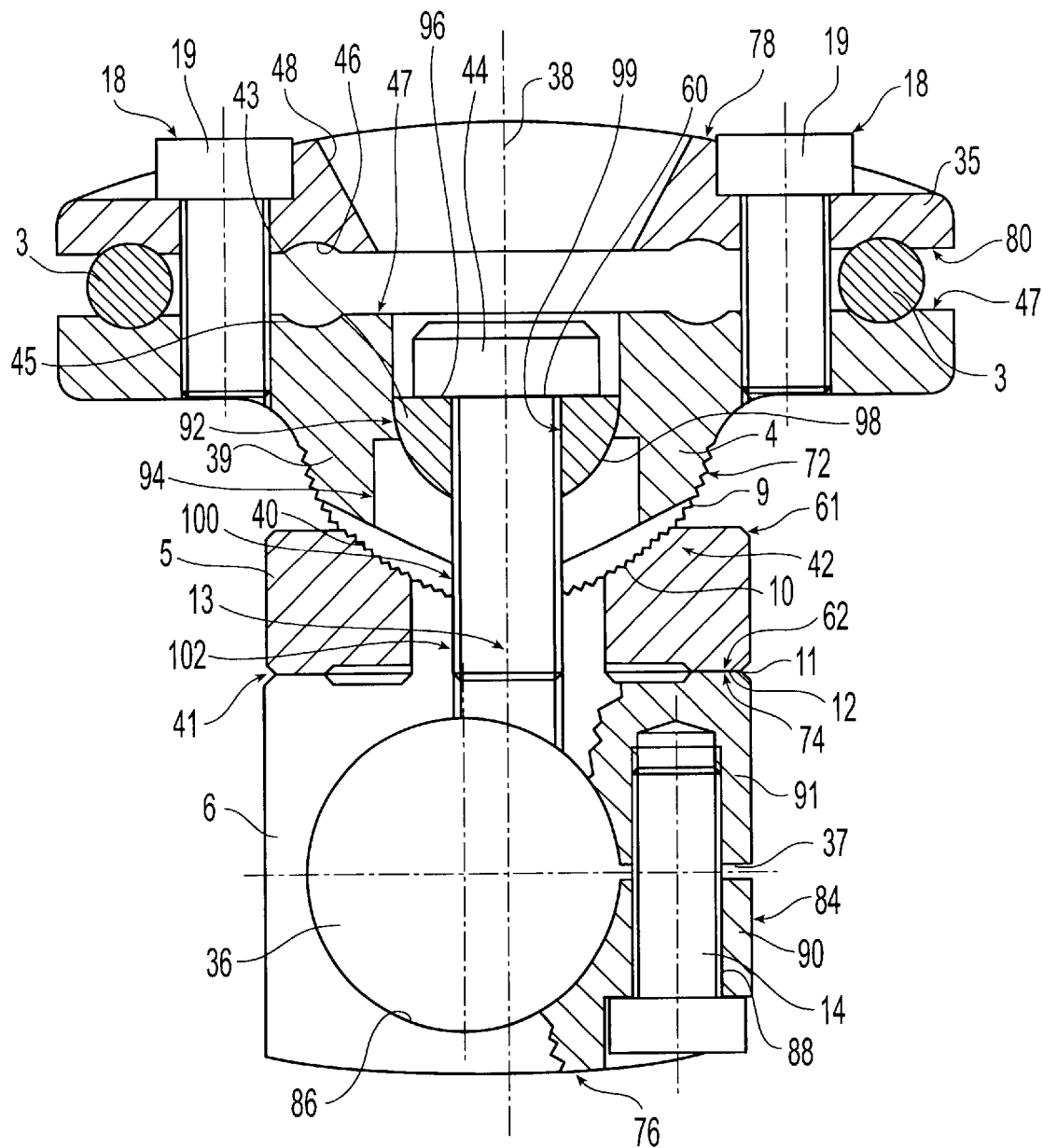
FIG. 2 is a partial cross-sectional view of a clamp assembly of FIG. 1.

The present invention is related to a device for traumatology and orthopedics for the external fixation of parts of broken bones. The device includes a jaw, as well as upper, middle, and lower elements mounted along one axis, hereafter the common axis, with bone screws or pins being affixable between the upper element and the clamping surface of the jaw. At least two bone screws may be clamped. The device as a whole is affixable to a longitudinal connecting element. The upper element pivots relative to the middle element about a swivelling axis running transverse to the common axis of the three elements, clampable against a first surface suitable as a swivel surface on the middle element transverse to the common axis, and fixable in a given position. The swivelling axis can run perpendicular to the common axis. The lower element is rotatable relative to the middle element about the common axis of the three elements and can be clamped in a desired position against a second surface of the middle element.

A borehole in the lower element has a borehole axis and extends transverse to the common axis of the three elements, and allows the lower element and consequently the device as a whole to be moved along the length of a connecting element. When the lower element is mounted on a connecting element, it is rotatable about the borehole axis and lockable in any position about the borehole axis with an affixation element such as a tightening screw. The relative movements of the elements are controlled by a tightening screw so that, when the tightening screw is tightened, the elements are mutually compressed at their contacting surfaces. The mutually contacting surfaces of the elements are serrated to confer positive locking between any two elements. In one embodiment, the swivel axis of the upper and middle elements is perpendicular to the common axis, while the borehole axis intersects the common axis of the elements. At least two of the elements have serrations at mutually contacting surfaces to establish a positive connection therebetween. All three elements are mutually affixable, and the device is affixable to the connecting element with no more than two affixation screws.

In a preferred embodiment, the middle element and the upper element have end faces that contact each other and are parallel to each other. Only a single tightening screw is needed to lock the three elements with respect to each other and clamp the lower element to the connecting element. The tightening screw has a head that can rest on a support surface perpendicular to the common axis, and the surface can be a surface of the lower element or the surface of an insert that further has an arcuate surface rotatably supported in the upper element. The tightening screw can be screwed into a matching thread in the insert or a matching thread in the lower element. Furthermore, the lower element can be fitted with a unilateral slit on one side of the element and extending the length of the borehole, and the tightening screw may permit the slit to be compressed to additionally compress the borehole and clamp the lower element in a desired position on the connecting element.

In another embodiment, the serrations on the contacting faces of the lower and middle elements are circular and concentric to the common axis. The recess of the middle element is arcuate and forms a semi-circular clearance with a swivelling axis transverse to the common axis. The mutually contacting surfaces of the upper element and middle element are serrated. The mutually contacting serrations on the surfaces of the middle and upper elements are provided in an arcuate recess and a semi-circular bay having an axis of rotation perpendicular to the common axis. Bone screws are clampable between the jaw and the upper element by fasteners, preferably tightening screws, that are independent of the fastening of the elements. The opposing clamping surfaces of the upper element and the jaw can include parallel and aligned recesses extending across their width to partly seat bone screws. In addition, the tightening screw can include at both ends a hexagonal socket, a slotted region such as in a phillips screw, or other means for receiving a tool for use in loosening and tightening the screw.

Referring to FIGS. 1–4, a device 2 is shown for mounting on a connecting element 1 and for clamping bone screws 3. As will be discussed, the device is movable on and about connecting element 1, but also may be releasably fixed to it. The device includes an upper element 4 with a top surface 47 and a bottom surface 72, a middle element 5 with a top surface 61 and a bottom surface 62, and a lower element 6 with a top surface 74 and a bottom surface 76. Together, upper, middle, and lower elements 4, 5, 6, respectively, permit clamped bone screws 3 to be moved in three degrees of freedom relative to connecting element 1. Device 2 also includes a jaw 35 with a top surface 78 and a bottom surface 80. Tightening screws 18 extend through aligned holes in jaw 35 and upper element 4, with the heads 19 resting on top surface 78, and when the tightening screws 18 are tightened such that bottom surface 80 of jaw 35 and top surface 47 of upper element 4 are drawn toward each other, bone screws 3 are clamped therebetween.

In the preferred embodiment, clamping bottom surface 80 of jaw 35 and clamping top surface 47 of upper element 4 include parallel grooves 46, 45 respectively, for accommodating bone screws 3. Grooves 46, 45 extend perpendicular to the plane of the page, across the length of surfaces 80, 47 respectively. Thus, when tightening screws 18 are tightened, bone screws 3 are firmly held in grooves 46, 45. Preferably, four parallel grooves are provided in jaw 35 and upper element 4.

Element 6 forms a base body that has a borehole 36 extending therethrough along a borehole axis 82 which extends perpendicular to the plane of the page. Borehole 36 is configured and dimensioned for receiving connecting element 1 which has a central axis 7. Preferably, the diameter of borehole 36 is chosen such that when element 6 is mounted on connecting element 1, element 6 and consequently the remainder of device 2 can be positioned longitudinally along connecting element 1, and also rotated thereon as shown generally by arrow B. In the preferred embodiment, element 6 includes a slit 37 extending the length of borehole 36 from side surface 84 to borehole surface 86 and defining element regions 90, 91. A fastener hole 88 is also included, and extends from bottom surface 76, connecting regions 90, 91 of element 6. An affixation screw 14 is disposed in fastener hole 88. When a desired orientation of device 2 is chosen on connecting element 1, screw 14 is tightened, thereby decreasing the separation of regions 90, 91 of element 6 due to slit 37 and detachably clamping device 2 to connecting element 1. Preferably, central axis 7 and borehole axis 82 generally coincide, and when screw 14 is loosened, the position and orientation of device 2 on connecting element 1 may be adjusted. In addition, elements 4, 5, 6 preferably are disposed about common axis 38 which preferably is perpendicular to central axis 7 and borehole axis 82. Jaw 35 is also preferably disposed about a common axis 38.

Element 5 is rotatable relative to element 6 about common axis 38, as shown generally with arrow C, such that a degree of rotational freedom is provided to device 2. The contacting surfaces 62 and 74 between middle and lower elements 5, 6, respectively, are serrated and form a clamping connection 41. Serrations 11 of middle element 5 and serrations 12 of lower element 6 engage each other, and when elements 5 and 6 are tightened against each other, serrations 11, 12 cause positive locking of elements 5 and 6 with respect to each other. Preferably, serrations 11, 12 are radially disposed about common axis 38.

Element 4 swivels with respect to element 5 about a swivel axis transverse to common axis 38, as generally shown with arrow D. Bottom surface 72 of upper element 4 and top surface 61 of middle element 5 are arcuate. Preferably, a semicircular portion 39 of bottom surface 72 is received in a like-formed recessed portion 40 of top surface 61. Engagement of portions 39, 40 allows swivelling such that another degree of freedom is provided for device 2. The contacting surfaces 72, 61 of upper and middle elements 4, 5, respectively, are serrated and form a clamping connection 42. Mutually positively locking serrations 9, 10 limit relative movement of elements 4, 5 with respect to each other when elements 4, 5 are tightened against each other. Preferably, serrations 9, 10 are radially disposed about common axis 38.

In the preferred embodiment, the two clamping connections 41, 42 are fixable by a single affixation element in the form of an affixation screw 13. Preferably, upper element 4 includes a central arcuate region 92 and a slotted region 94. In one embodiment, an insert 43 is disposed in central arcuate region 92. Insert 43 has a top surface 96, an arcuate bottom surface 98, and a central hole 99 extending therethrough. Bottom surface 98 is configured and dimensioned to rest in central arcuate region 92 of upper element 4. Holes 100, 102 extend through middle and lower elements 5, 6, respectively, and when a screw 13 extends through holes 99, 100, 102, the holes are coaxially disposed about central axis 38. Head 44 of screw 13 rests on top surface 96 of insert 43 and threaded shank 97 extends through holes 99, 100, 102. Preferably, hole 102 in lower element 6 is threaded, and threadably receives shank 97. Upper element 4 is permitted to swivel with respect to middle element 5 until screw 13 is tightened so that serrated surfaces 61, 72 are engaged, and similarly serrated surfaces 62, 74 are engaged, to cause positive locking. During swivelling, screw 13 remains in alignment with common axis 38, and upper element 4 swivels, in part, through the clearance created by slotted region 94 around screw 13.

Jaw 35 further includes an aperture 48 allowing tightening or loosening of affixation element 13 even when jaw 35 is firmly secured to element 4 and bone screws 3 are clamped therebetween. Thus, when device 2 is mounted on a connecting element 1, firmly clamped bone screws 3 still may be oriented relative to connecting element 1 in two degrees of freedom provided at the two clamping connections 41, 42 by loosening the single affixation element 13.

Figure 3:
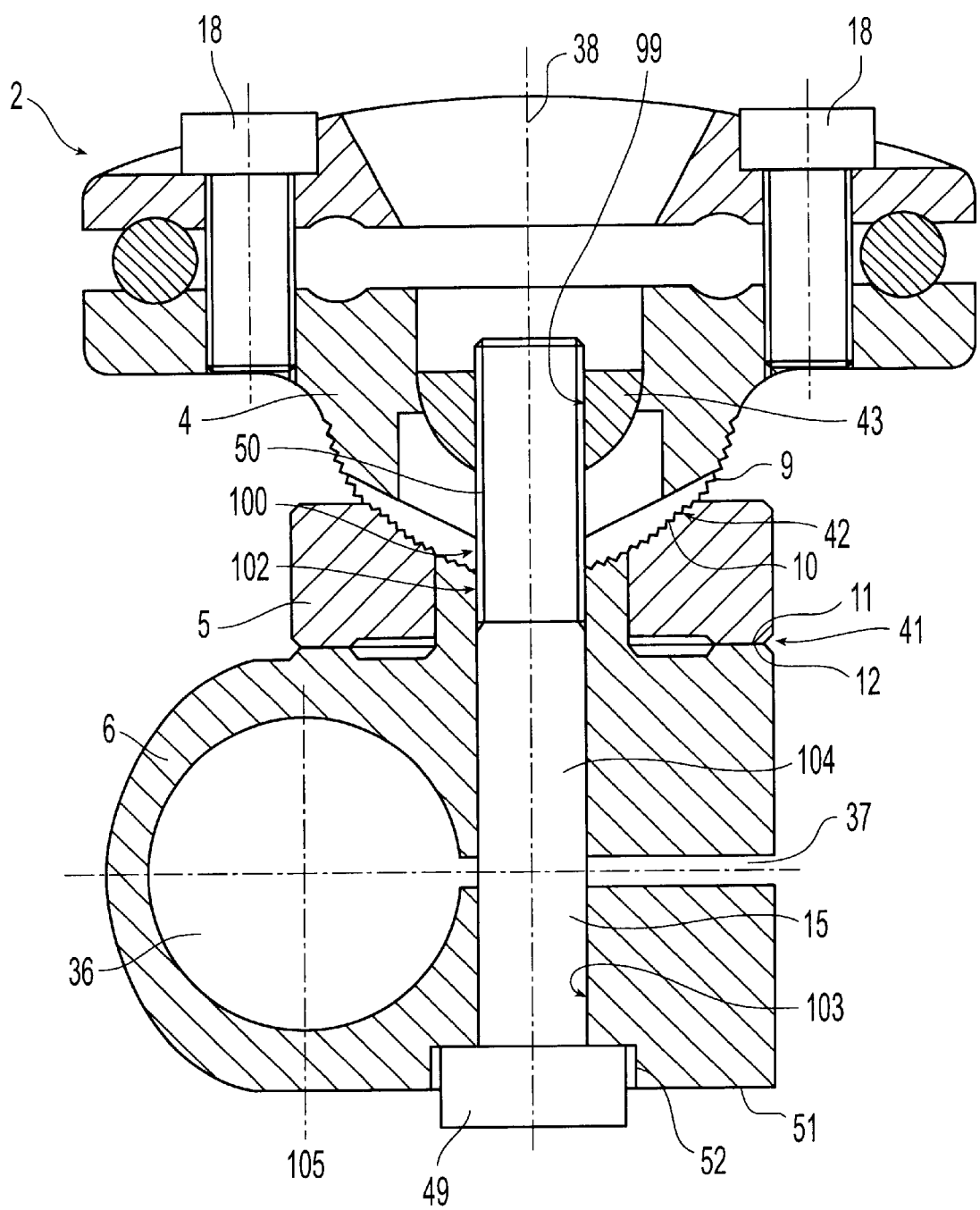
FIG. 3 is a cross-sectional view of another embodiment of a clamp assembly of the present invention.

In another embodiment of device 2 shown in FIG. 3, a single affixation element 15 in the form of a tightening screw is mounted between element 6 and an insert 43 disposed in element 4. Preferably, tightening screw 15 is disposed along common axis 38, and screw head 49 of tightening screw 15 rests in a counterbore 52 in lower end 51 of lower element 6. Furthermore, shank 104 extends through holes 99, 100, 102, 103. Preferably, hole 99 in insert 43 is threaded, and threadably receives threaded portion 50 of shank 97 of tightening screw 15. Thus, tightening screw 15 fixes all three elements 4, 5, 6 in place. As previously described, tightening screw 15 extends through a slit 37 which runs the length of borehole 36. Preferably, borehole 36 is disposed about a borehole axis 106, which extends perpendicular to the plane of the page.

When a desired orientation of device 2 is chosen on a connecting element 1, screw 15 is tightened to compress slit 37, and device 2 is detachably clamped to connecting element 1. At the same time, tightening of screw 15 locks both the clamping connection 41 between elements 5 and 6 through the mutually positively locking serrations 11 and 12, respectively, and also locks the clamping connection 42 between elements 4 and 5 through mutually positively locking serrations 9 and 10. Preferably, central axis 7 and borehole axis 106 generally coincide, and when screw 15 is loosened, the position and orientation of device 2 on connecting element 1 may be adjusted. Borehole 36 is centered about an axis 105 that is parallel to and offset from common axis 38. Three degrees of freedom of movement can be arrested with tightening screw 15.

Figure 4:
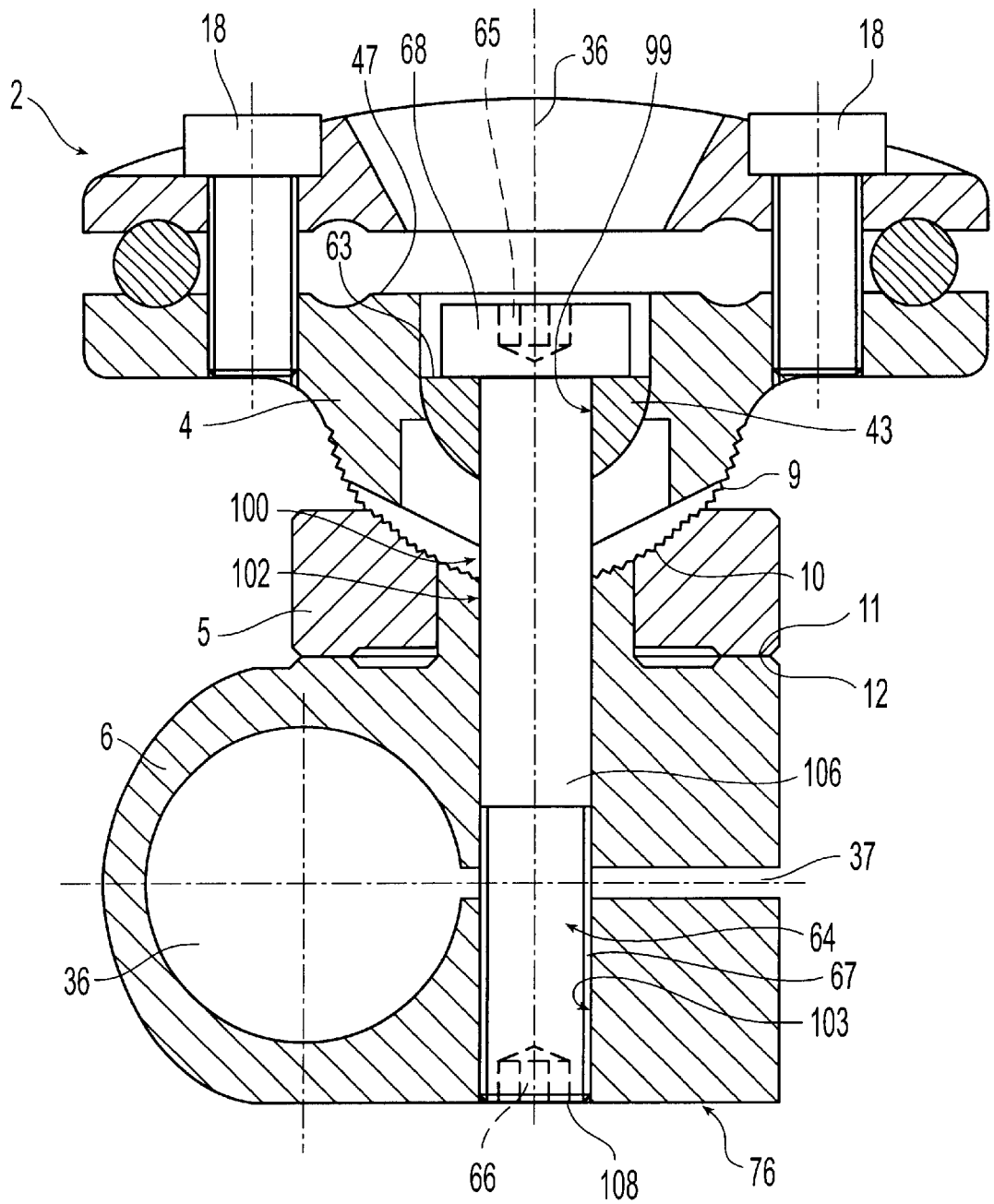
FIG. 4 is a cross-sectional view of a further embodiment of a clamp assembly of the present invention.

Another embodiment of device 2 is shown in FIG. 4, with an affixation element 64 in the form of an affixation screw mounted between lower element 6 and an insert 43 disposed in upper element 4. Preferably, affixation screw 64 is disposed along common axis 38. The head 68 of screw 64 rests on arcuate insert 43 rotatably supported in the element 4, and shank 106 extends through holes 99, 100, 102, 103 and is preferably threadably received in threaded region 67 in lower element 6. In this embodiment, head 68 and lower portion 108 of screw 64 are configured and dimensioned to receive a tool to loosen or tighten screw 64. Preferably, a hexagonal socket is provided in head 68 and lower portion 108, permitting screw 64 to be accessed and tightened or loosened from the bottom surface 76 of element 6 as well as from the top surface 47 of upper element 4.

Advantageously, device 2 includes positively locking, affixable articulations for use in orienting bone screws with respect to a longitudinal connecting element. The articulation integrated with device 2 permits two or three degrees of freedom in movement to be arrested using a single affixation screw.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. For example, in an alternate embodiment, tightening screws 18 may include both a head and lower shank portion that are configured and dimensioned for receiving a tool for loosening or tightening of the clamping action of jaw 35 and upper element 4. In addition, central arcuate region 92 of upper element 4 and arcuate bottom surface 98 of insert 43 may be serrated to permit positive locking. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. An external bone fixation system for clamping bone pins and a connecting element, the system comprising a jaw having top and bottom surfaces, an upper element having top and bottom surfaces, the jaw and upper element being configured and dimensioned for retaining bone pins therebetween, a middle element having top and bottom surfaces, and a lower element having top and bottom surfaces, the elements being disposed about a common axis, wherein the upper element can swivel relative to the middle element about a swivelling axis transverse to the common axis, and the bottom surface of the upper element is clampable against the top surface of the middle element, the middle element can rotate relative to the lower element about the common axis and the bottom surface of the middle element is clampable against the top surface of the lower element, the lower element having a borehole extending therethrough and being demountably attachable to and rotatable about the connecting element, wherein opposing surfaces of at least two of the elements are positively engageable, the upper, middle, and lower elements are coupled by a common fastener disposed along the common axis while the jaw and upper element are coupled by at least one fastener that is not disposed on the common axis.

2. The external bone fixation system of claim 1, wherein the common axis is disposed substantially perpendicular to the swivelling axis.

3. The external bone fixation system of claim 1, wherein the borehole in the lower element is disposed transversely to the common axis.

4. The external bone fixation system of claim 1, wherein the top and bottom surfaces of the middle element are substantially parallel.

5. The external bone fixation system of claim 1, wherein the common fastener that couples the upper, middle, and lower elements further releasably fixes the lower element to the connecting element.

6. The external bone fixation system of claim 1, wherein the upper element includes a recessed portion with an insert seated therein, and the common fastener threadably engages at least one of the insert and the lower element.

7. The external bone fixation system of claim 1, wherein the bottom surface of the upper element is curved and is received in a recess in the top surface of the middle element.

8. The external bone fixation system of claim 7, wherein the bottom surface of the upper element and the recess in the top surface of the middle element include mutually positively locking serrations which lock the upper and middle elements in any one of a plurality of swivelled positions.

9. The external bone fixation system of claim 8, wherein the serrations are radially disposed about the common axis.

10. The external bone fixation system of claim 7, wherein the top surface of the lower element and the bottom surface of the middle element include mutually positively locking serrations which lock the lower and middle elements in any one of a plurality of rotational positions.

11. The external bone fixation system of claim 10, wherein the serrations are radially disposed about the common axis.

12. The external bone fixation system of claim 1, wherein the lower element includes a fastener for demountably attaching that element to the connecting element.

13. The external bone fixation system of claim 1, wherein the borehole of the lower element is disposed about a central borehole axis that is offset from and transverse to the common axis.

14. The external bone fixation system of claim 13, wherein the lower element has a fastener hole aligned with the common axis and which includes threads for engaging the threads of the common fastener.

15. The external bone fixation system of claim 13, wherein the upper element has a fastener hole aligned with the common axis and which includes threads for engaging the threads of the common fastener.

16. The external bone fixation system of claim 1, wherein said common fastener arrests two degrees of freedom.

17. The external bone fixation system of claim 1, wherein said common fastener arrests three degrees of freedom.

18. The external bone fixation system of claim 17, wherein said common fastener has a first end and a second end and is configured and dimensioned to be engaged at either end to permit screwing action thereof.

19. An external bone fixation system for clamping bone pins and a connecting element, the system comprising a first element having top and bottom surfaces, a second element having top and bottom surfaces, the first and second elements being configured and dimensioned for retaining bone pins therebetween, a third element having top and bottom surfaces, and a fourth element having top and bottom surfaces, wherein the second, third, and fourth elements are coupled by a common fastener disposed along a common axis, and the first and second elements are coupled by at least one fastener remote from the common axis, the second and third elements can swivel with respect to each other to be generally oriented transverse to the common axis, and the third and fourth elements can rotate with respect to each other about the common axis, the bottom surface of the second elememt is clampable against the top surface of the third element, and bottom surface of the third element is clampable against the top surface of the fourth element, and the fourth element includes a borehole extending therethrough for receiving the connecting element.

20. The external bone fixation system of claim 19, wherein opposing surfaces of at least two of the elements are positively engageable.

21. The external bone fixation system of claim 19, wherein the borehole in the fourth element is disposed transversely to the common axis.

22. The external bone fixation system of claim 19, wherein the top and bottom surfaces of the third element are substantially parallel.

23. The external bone fixation system of claim 19, wherein the common fastener that couples the second, third, and fourth elements further releasably fixes the fourth element to the connecting element.

24. The external bone fixation system of claim 19, wherein the second element includes a recessed portion with an insert seated therein, and the common fastener threadably engages at least one of the insert and the fourth element.

25. The external bone fixation system of claim 19, wherein the bottom surface of the second element is curved and is received in a recess in the top surface of the third element.

26. The external bone fixation system of claim 25, wherein the bottom surface of the second element and the recess in the top surface of the third element include mutually positively locking serrations which lock the second and third elements in any one of a plurality of swivelled positions.

27. The external bone fixation system of claim 26, wherein the serrations are radially disposed about the common axis.

28. The external bone fixation system of claim 25, wherein the top surface of the fourth element and the bottom surface of the third element include mutually positively locking serrations which lock the fourth and third elements in any one of a plurality of rotational positions.

29. The external bone fixation system of claim 28, wherein the serrations are radially disposed about the common axis.

30. The external bone fixation system of claim 19, wherein the fourth element includes a fastener for demountably attaching that element to the connecting element.

31. The external bone fixation system of claim 19, wherein the borehole of the fourth element is disposed about a central borehole axis that is offset from and transverse to the common risk.

32. The external bone fixation system of claim 31, wherein the second element has a fastener hole aligned with the common axis and which includes threads for engaging the threads of the common fastener.

33. The external bone fixation system of claim 31, wherein the second element has a fastener hole aligned with the common axis and which includes threads for engaging the threads of the common fastener.

34. The external bone fixation system of claim 19, wherein said common fastener arrests two degress of freedom.

35. The external bone fixation system of claim 19, wherein said common fastener arrests three degrees of freedom.

36. The external bone fixation system of claim 35, wherein said common fastener has a first end and a second end and is configured and dimensioned to be engaged at either end to permit screwing action thereof.

37. The external bone fixation system of claim 19, wherein said fourth element is rotatable about the connecting element.

\* \* \* \* \*

UNITED STATES PATENT AND TRADEMARK OFFICE
CERTIFICATE OF CORRECTION

PATENT NO. : 6,409,729 B1
DATED : June 25, 2002
INVENTOR(S) : Martinelli et al.

It is certified that error appears in the above-identified patent and that said Letters Patent is hereby corrected as shown below:

Column 9,
Line 15, replace "risk" with -- axis --;
Line 17, replace "second" with -- fourth --.

Signed and Sealed this

Tenth Day of September, 2002

Attest:

JAMES E. ROGAN
Attesting Officer
Director of the United States Patent and Trademark Office